US012544206B2

(12) United States Patent
Zhang

(10) Patent No.: US 12,544,206 B2
(45) Date of Patent: Feb. 10, 2026

(54) PRE-FORMED PARASTOMAL HERNIA REINFORCEMENT MESH

(71) Applicant: Zhongqiu Zhang, Middlebury, CT (US)

(72) Inventor: Zhongqiu Zhang, Middlebury, CT (US)

( * ) Notice: Subject to any disclaimer, the term of this patent is extended or adjusted under 35 U.S.C. 154(b) by 0 days.

(21) Appl. No.: 18/479,023

(22) Filed: Sep. 30, 2023

(65) Prior Publication Data

US 2024/0024086 A1 Jan. 25, 2024

Related U.S. Application Data

(63) Continuation of application No. 17/356,125, filed on Jun. 23, 2021, now Pat. No. 11,779,448.

(51) Int. Cl.
*A61F 2/00* (2006.01)

(52) U.S. Cl.
CPC .... *A61F 2/0063* (2013.01); *A61F 2002/0068* (2013.01)

(58) Field of Classification Search
CPC ....................... A61F 2/0063; A61F 2002/0068
See application file for complete search history.

(56) References Cited

U.S. PATENT DOCUMENTS 4,854,316 A 8/1989 Davis
6,652,595 B1 * 11/2003 Nicolo .................. A61F 2/0063 623/23.72
2006/0089524 A1 * 4/2006 Chu ...................... A61F 2/0045 600/37
2008/0167729 A1 7/2008 Nelson
2011/0231452 A1 9/2011 Nakajima et al.
2013/0253645 A1 * 9/2013 Kerr .......................... A61F 2/12 623/8
2015/0094743 A1 4/2015 Russo
2015/0250574 A1 * 9/2015 Egnelov .................... A61F 2/12 606/151
2015/0297798 A1 10/2015 Badylak

FOREIGN PATENT DOCUMENTS

WO WO-2020193292 A1 * 10/2020 ........... A61F 2/0063

OTHER PUBLICATIONS

Hansson, B.M.E., Morales-Conde, S., Mussack, T. et al. The laparoscopic modified Sugarbaker technique is safe and has a low recurrence rate: a multicenter cohort study. Surg Endosc 27, 494-500 (2013) (Year: 2012).*
Gillern, S, Bleier, J., “Parastomal Hernia Repair and Reinforcement: The Role of Biologic and Synthetic Materials,” Thieme Medical Publishers, Inc., 2014.
Sugarbaker, P., “Peritoneal Approach to Prosthetic Mesh Repair of Paraostomy Hernias,” Annals of Surgery, vol. 20, No. 3, 1984.

* cited by examiner

*Primary Examiner* — Jing Rui Ou
(74) *Attorney, Agent, or Firm* — Hinckley Allen & Snyder; Stephen Holmes

(57) ABSTRACT

A mesh for repair/prevention of a parastomal hernia during ostomy treatment is disclosed. More specifically, a pre-molded mesh having a unique shape to provide support to the abdominal wall adjacent a stoma formed during an ostomy procedure to prevent/repair formation of a parastomal hernia is disclosed which also provides a clearance channel through which the bowel can pass in a manner that prevents collapse or obstruction of the exposed segment of the bowel.

10 Claims, 1 Drawing Sheet

PRE-FORMED PARASTOMAL HERNIA REINFORCEMENT MESH

CROSS-REFERENCE TO RELATED APPLICATIONS

This application is a continuation of U.S. application Ser. No. 17/356,125, filed Jun. 23, 2021.

BACKGROUND OF THE DISCLOSURE

The present disclosure relates generally to a mesh for repair/prevention of a parastomal hernia during ostomy treatment. More specifically, the present disclosure relates to a pre-molded mesh having a unique shape to provide support to the abdominal wall adjacent a stoma formed during an ostomy procedure to prevent/repair formation of a parastomal hernia while also providing a clearance channel through which the bowel can pass in a manner that prevents collapse or obstruction of the exposed segment of the bowel.

A parastomal hernia occurs when the intestines press outward through a stoma, the hole created for a colostomy or ileostomy appliance. This results in the formation of a bulge under the skin that can also cause pain and bothersome leakage. Parastomal hernias are the most common complication of ostomy surgery. Between 87,000 and 135,000 intestinal stomas are formed in patients each year, The fundamental problem is that the ostomy creation introduces an abdominal wall defect for which no healing is expected and the parastomal hernia forms because the abdominal wall is continually stretched by forces tangential to its circumference. In approximately half of ostomy patients, parastomal hernias develop as a complication that often requires surgical repair.

While stoma closure is the best option, often it is not feasible when the stoma is needed to maintain ostomy treatment. Primary suture repair of the hernia site adjacent the stoma has an unacceptably high recurrence rate and stoma re-siting often results in three hernias, with a hernia at the previous stoma site, one at the midline incision and one at the new stoma site. As a result, mesh repair has become a frequently utilized solution, where an onlay mesh approach is the primary technique. The onlay approach often allows for easy hernia reduction but may be associated with difficult adhesiolysis and results in a large peri-wound cavity. Wound complications are a concern and post-operative stoma care can be difficult for the patient to maintain resulting in increased infection risk. A midline approach to an onlay repair may be difficult in an obese patient and there may be devascularization due to creation of large tissue flaps.

The most common mesh repairs are done in the sublay and intraperitoneal positions that place the mesh below the anterior fascia. The advantage of a sublay repair is that it is performed in a sterile environment with a decreased risk of wound infection. Sublay and intraperitoneal placement of the mesh provides more biomechanical support due to the abdominal pressure further securing the mesh to the abdominal wall. While the sublay repair protects the mesh from interaction with abdominal organs, the intraperitoneal position poses an increased risk for bowel erosion and adhesion formation. In the intraperitoneal repair, care must be taken to maximize tissue apposition between the mesh and the abdominal wall to minimize the formation of seroma. This includes liberal use of closed suction drains placed between the mesh and the abdominal wall. In the sublay approach, alterations must be made to the basic technique to accommodate the stoma.

There are two primary techniques for intraperitoneal mesh repair, the Sugarbaker technique and the keyhole technique. In the Sugarbaker technique, after the hernia was reduced and the stoma trephine reduced to appropriate size, the ostomy opening is covered with an intraperitoneally placed prosthetic mesh that is sutured to the fascia. The bowel is lateralized and secured between the mesh and the peritoneum, thereby lateralizing the forces which press the bowel ventrally onto the abdominal wall. Complications of the procedure included bowel obstruction secondary to dense adhesions, wound infection, seroma formation, and pain at the site of transfascial sutures.

The other primary option for surgical repair is the keyhole technique. In the keyhole technique, a cut-out of mesh is made to circumferentially surround the ostomy and cover the entire hernia defect. One of the tricks of this technique is to not make the keyhole too small so as to cause a bowel obstruction, but to not make it so large as to increase the risk of herniation.

Generally, there is a movement towards prophylactic placement of reinforcement mesh for the prevention of the formation of parastomal hernias during ostomy treatment. It is known that the solid piece of mesh utilized in the Sugarbaker repair is more reliable than a keyhole repair with a cut mesh in that hernia recurrence with a Sugarbaker repair is 12% while a keyhole repair results in a recurrence rate of around 35%. However, issues still arise revolving around the technique as well as type and size of mesh, what size hole, and how should it best be secured in place. Utilizing the existing techniques is still seen to result in collapsing of the bowel with resulting obstructions as well as mesh migration.

SUMMARY OF THE DISCLOSURE

There is therefore a need for a repair mesh for use in repairing/preventing a parastomal hernia during ostomy treatment. There is a further need for a pre-molded repair mesh for use in repairing/preventing a parastomal hernia during ostomy treatment that resists migration and allows placement without risking collapse or blockage of the extended bowel section.

In this regard, the present disclosure provides a mesh for repair/prevention of a parastomal hernia during ostomy treatment. More specifically, a pre-molded mesh having a unique shape to provide support to the abdominal wall adjacent a stoma formed during an ostomy procedure to prevent/repair formation of a parastomal hernia is disclosed which also provides a clearance channel through which the bowel can pass in a manner that prevents collapse or obstruction of the exposed segment of the bowel.

In accordance with the present disclosure a prosthesis mesh patch is disclosed as an improvement for the Sugarbaker repair technique. In the Sugarbaker technique, the parastomal hernia repair is performed via a laparotomy. The herniated opening in the abdominal wall is covered with an intraperitoneally placed prosthetic mesh that is sutured to the fascial edge. The bowel is lateralized, passing from the hernia sac between the abdominal wall and the prosthesis into the peritoneal cavity. It is known from incisional hernia repair, that an overlap of 2.5-5 cm between the mesh and the adjacent fascia is mandatory to prevent recurrent hernias. Therefore, the Sugarbaker technique was modified around the trephine opening to guarantee an adequate overlap between the mesh and the fascia.

It is of utmost importance to prevent narrowing of the bowel in the tunnel and angulation of the bowel when entering the abdominal cavity and the hernia sac. In this regard, the region to be repaired is covered with a mesh patch that is relatively stiff and rigid. As the flat mesh is placed it must be shaped and bent as it is stitched to the trephine to prevent its normally flat nature from compressing the bowel and causing obstruction.

In accordance with the present disclosure, a mesh repair prosthetic is provided that is uniquely shaped during manufacture or prior to the procedure. The mesh is preformed, or heat molded to create a raised central region that creates a preformed tunnel on the distal surface of the mesh. The tunnel in turn serves to assist in correctly positioning the repair prosthesis over the lateralized bowel as well as creating the needed clearance for the bowel to pass through the stoma without compression or obstruction thereof.

It is therefore an object of the present disclosure to provide a repair mesh for use in repairing/preventing a parastomal hernia during ostomy treatment. It is a further object of the present disclosure to provide a pre-molded repair mesh for use in repairing/preventing a parastomal hernia during ostomy treatment that resists migration and allows placement without risking collapse or blockage of the extended bowel section.

It is still a further object of the present disclosure to provide a pre-molded repair mesh for use in repairing/preventing a parastomal hernia during ostomy treatment reduces the time previously needed to form the mesh as it is installed during the procedure that further assists in prosthesis placement without risking collapse or blockage of the extended bowel section.

These together with other objects of the invention, along with various features of novelty which characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWING FIGURES

In the drawings which illustrate the best mode presently contemplated for carrying out the present invention:

DETAILED DESCRIPTION OF THE EXEMPLARY EMBODIMENTS

Certain exemplary embodiments will now be described to provide an overall understanding of the principles of the structure, function, manufacture, and use of the device and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure. Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Further, to the extent that directional terms like top, bottom, up, or down are used, they are not intended to limit the systems, devices, and methods disclosed herein. A person skilled in the art will recognize that these terms are merely relative to the system and device being discussed and are not universal.

Figure 1:
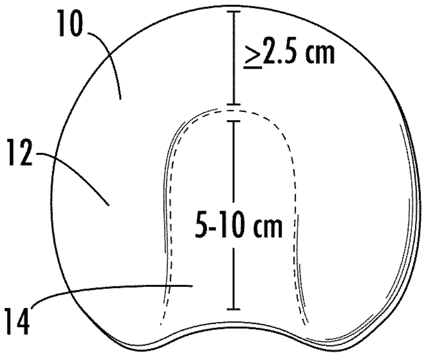
FIG. 1 is a proximal view of a mesh repair prosthesis in accordance with the present disclosure.

Now referring to the drawings, the preformed prosthetic repair mesh for a parastomal hernia repair is shown and generally illustrated in the figures. As can be seen in FIG. 1, a preformed mesh prosthetic 10 is disclosed for repair/prevention of a parastomal hernia during ostomy treatment. More specifically, the preformed mesh prosthetic 10 has a unique shape including blunted or rounded edges to improve placement and increase the biocompatibility of the preformed mesh prosthetic 10. The includes a margin region 12 that is preferably greater than or equal to 2.5 cm in width to provide support to the abdominal wall adjacent a stoma formed during an ostomy procedure to prevent/repair formation of a parastomal hernia and to provide sufficient overlap onto the adjacent fascia to provide effective repair and prevent formation of additional hernias.

In addition, the preformed mesh prosthetic 10 includes a preformed clearance channel 14 through which the bowel can pass in a manner that prevents collapse or obstruction of the exposed segment of the bowel. The preformed clearance channel 14 is formed in the preformed mesh prosthetic 10 having a size and shape to accommodate the protrusion of the lateralized bowel such that support is provided to the facia adjacent the stoma and yet no pressure is exerted onto the bowel thereby preventing collapsing or obstruction of the bowel that passes therethrough. The extension length of the preformed clearance channel 14 is preferably between 5 cm and 10 cm in length and has a smooth rounded shape and transitions so as to improve placement and increase the biocompatibility of the preformed mesh prosthetic 10.

Figure 2:
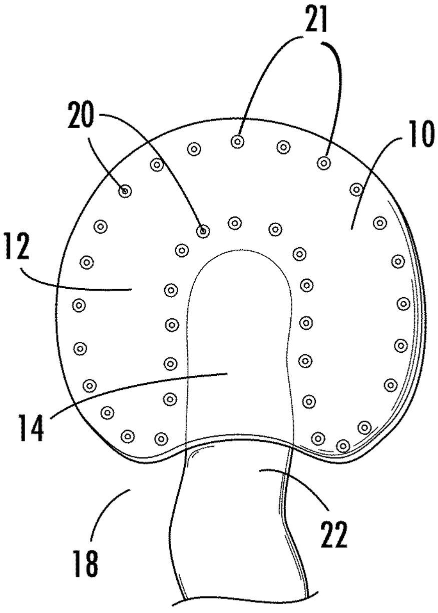
FIG. 2 is a proximal view of a mesh repair prosthesis positioned over the lateralized bowel adjacent the stomal opening in accordance with the present disclosure.
Figure 3:
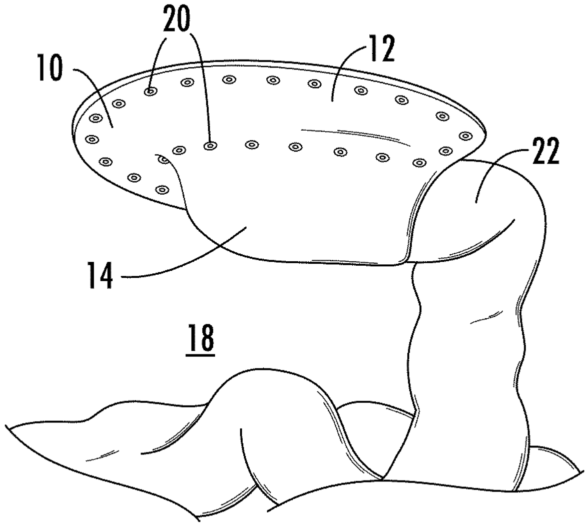
FIG. 3 is a lateral perspective view of a mesh repair prosthesis positioned over the lateralized bowel adjacent the stomal opening in accordance with the present disclosure.
Figure 4:
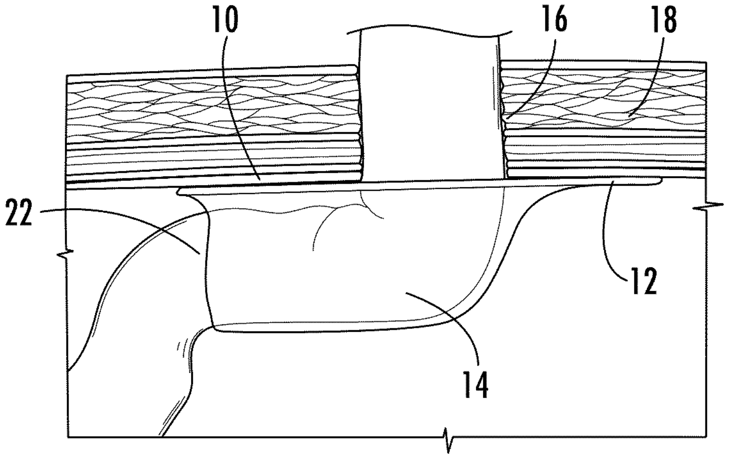
FIG. 4 is a partial cross-sectional view of a mesh repair prosthesis positioned over the lateralized bowel adjacent the stomal opening in accordance with the present disclosure.

Turning now to FIGS. 2-4, in accordance with the present disclosure, the preformed mesh prosthetic 10 is disclosed as a modification for the Sugarbaker repair technique. In the Sugarbaker technique the parastomal hernia repair is performed via a laparotomy. The herniated region adjacent the stomal opening 16 in the abdominal wall 18 is covered with an intraperitoneally placed preformed mesh prosthetic 10 that is attached to the fascial edge using sutures. The preformed mesh prosthetic 10 may include preformed openings 20 to facilitate placement of sutures for fastening to the trephine. Further, the preformed openings may include reinforcement rings 21 to increase the durability of the preformed mesh prosthetic 10. The openings are preferably positioned about the outer margin of the preformed mesh prosthetic 10 and at the transition between the margin region 12 and the preformed clearance channel 14.

The lateralized bowel 22, passes from the hernia sac between the abdominal wall and the preformed mesh prosthetic 10 into the peritoneal cavity. As stated previously, it is known from incisional hernia repair, that an overlap of 2.5-5 cm between the preformed mesh prosthetic 10 and the adjacent abdominal wall 18 fascia is mandatory to prevent recurrent hernias.

Given that it is of utmost importance to prevent narrowing of the bowel in the tunnel and angulation of the bowel when entering the abdominal cavity and the hernia sac, the region to be repaired is covered with the preformed mesh prosthetic 10. In the prior art the relatively stiff and rigid mesh is flat and it must be shaped and bent as it is stitched to the trephine to prevent its normally flat nature from compressing the bowel and causing obstruction.

In accordance with the present disclosure, a preformed mesh prosthetic 10 is provided that is shaped during manufacture or prior to the procedure. The preformed clearance channel 14, in turn, serves to assist in correctly positioning the preformed mesh prosthetic 10 over the lateralized bowel as well as creating the needed clearance for the bowel to pass through the stoma without compression or obstruction thereof.

The preformed mesh prosthetic 10 of the present disclosure is preferably formed to have a mesh matrix using a material selected from the group consisting of the following materials: synthetic mesh such as polypropylene, polyester, ePTFE; bioabsorbable; bio-sourced tissue or combinations thereof. Further, the mesh may be coated with absorbable fatty acids, cellulose or collagen to prevent adhesions thereto. The unique shape of the preformed mesh prosthetic 10 is preferable performed during the mesh manufacture either by shaping the mesh as it is formed/woven or by heat molding the mesh. Further, the preformed mesh prosthetic 10 may be shaped using heat molding by the surgeon prior to the procedure.

It can therefore be seen that the present disclosure provides a repair mesh for use in repairing/preventing a parastomal hernia during ostomy treatment. The present disclosure further provides a pre-molded repair mesh for use in repairing/preventing a parastomal hernia during ostomy treatment that resists migration and allows placement without risking collapse or blockage of the extended bowel section. Still further, the present disclosure provides a pre-molded repair mesh for use in repairing/preventing a parastomal hernia during ostomy treatment reduces the time previously needed to form the mesh as it is installed during the procedure that further assists in prosthesis placement without risking collapse or blockage of the extended bowel section. For these reasons, the present disclosure is believed to represent a significant advancement in the art, which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed:

1. A preformed parastomal hernia reinforcement prosthetic, comprising:

a one-piece, unitary, bio-implantable, heat-formable pre-molded mesh sheet having a generally circular shape and an upper surface, said pre-molded mesh sheet including an elongated clearance channel pre-formed in said upper surface thereof and extending from a central portion thereof to a peripheral edge thereof and wherein the clearance channel has a closed end adjacent the central portion of the mesh sheet and an open end at the peripheral edge, said clearance channel being pre-formed and configured to be positioned about a lateralized bowel segment positioned adjacent a herniated area of an abdominal wall, said pre-molded mesh sheet further including a U-shaped planar margin region pre-formed about a periphery of said clearance channel, the upper surface of the margin region being configured to be positioned adjacent and fastened to said herniated area of said abdominal wall surrounding a stomal opening therein, said pre-molded mesh sheet comprising a plurality of preformed suture attachment openings positioned about a periphery of said margin region and at a transition between said margin region and said clearance channel, said pre-formed suture attachment openings each including a reinforcement ring to improve durability, said pre-molded mesh sheet comprising a relatively stiff and rigid mesh which provides a relatively rigid and stiff abdominal wall support while also providing a relatively rigid and stiff clearance channel to support said lateralized bowel segment relative to the abdominal wall without compression thereof and which prevents collapse or obstruction of the lateralized bowel segment.

2. The preformed parastomal hernia reinforcement prosthetic of claim 1, wherein said margin region has a width of 2.5 cm or greater.

3. The preformed parastomal hernia reinforcement prosthetic of claim 1, wherein said clearance channel has a length of between 5 cm and 10 cm.

4. The preformed parastomal hernia reinforcement prosthetic of claim 1, wherein said clearance channel is formed in said bio implantable mesh sheet during manufacture thereof.

5. The preformed parastomal hernia reinforcement prosthetic of claim 1, wherein said clearance channel is formed in said bio implantable mesh sheet by heat molding.

6. The preformed parastomal hernia reinforcement prosthetic of claim 1, wherein said clearance channel is formed in said bio implantable mesh sheet prior to an implantation procedure.

7. The preformed parastomal hernia reinforcement prosthetic of claim 1, wherein said mesh sheet is a synthetic mesh material.

8. The preformed parastomal hernia reinforcement prosthetic of claim 1, wherein said mesh sheet is a bio sourced mesh material.

9. The preformed parastomal hernia reinforcement prosthetic of claim 1, wherein said mesh sheet is selected from the group consisting of: synthetic mesh, composite mesh, polypropylene, polyester, ePTFE, bioabsorbable mesh, biosourced tissue and combinations thereof.

10. The preformed parastomal hernia reinforcement prosthetic of claim 1, wherein said mesh sheet is coated with a material selected from the group consisting of:

absorbable fatty acids, cellulose or collagen and combinations thereof.

* * * * *